United States Patent
Hays et al.

(10) Patent No.: US 10,526,579 B2
(45) Date of Patent: Jan. 7, 2020

(54) PODOCYTE CULTURES AND USES THEREOF

(71) Applicant: RUSH UNIVERSITY MEDICAL CENTER, Chicago, IL (US)

(72) Inventors: Tristan Hays, Seminole, FL (US); Jochen Reiser, Hinsdale, IL (US); Vineet Gupta, Pinecrest, FL (US)

(73) Assignee: Rush University Medical Center, Chicago, IL (US)

( * ) Notice: Subject to any disclaimer, the term of this patent is extended or adjusted under 35 U.S.C. 154(b) by 931 days.

(21) Appl. No.: 14/767,104

(22) PCT Filed: Mar. 10, 2014

(86) PCT No.: PCT/US2014/022497
§ 371 (c)(1),
(2) Date: Aug. 11, 2015

(87) PCT Pub. No.: WO2014/150178
PCT Pub. Date: Sep. 25, 2014

(65) Prior Publication Data
US 2015/0376575 A1  Dec. 31, 2015

Related U.S. Application Data

(60) Provisional application No. 61/798,385, filed on Mar. 15, 2013.

(51) Int. Cl.
*C12N 5/071* (2010.01)
*G01N 33/50* (2006.01)
*G01N 33/569* (2006.01)

(52) U.S. Cl.
CPC ......... *C12N 5/0686* (2013.01); *C12N 5/0687* (2013.01); *G01N 33/502* (2013.01);
(Continued)

(58) Field of Classification Search
CPC .. C12N 5/0686; C12N 5/0687; G01N 33/502; G01N 33/5023; G01N 33/5026;
(Continued)

(56) References Cited

U.S. PATENT DOCUMENTS

| 2010/0178297 A1 | 7/2010 | Carmeliet et al. |
| 2011/0135574 A1 | 6/2011 | Greka |

(Continued)

FOREIGN PATENT DOCUMENTS

| WO | WO2011/073793 | 6/2011 | |
| WO | WO-2011073793 A1 * | 6/2011 | ........... C12N 5/0686 |

(Continued)

OTHER PUBLICATIONS

Saleem et al., A conditionally immortalized human podocyte cell line demonstrating nephrin and podocin expression. J Am Nephrol, vol. 13 (2002) pp. 630-638. (Year: 2002).*

(Continued)

*Primary Examiner* — Kara D Johnson
(74) *Attorney, Agent, or Firm* — Brinks Gilson & Lione

(57) ABSTRACT

The following disclosure generally relates to methods of culturing podocytes in vitro. The cultures can be used for drug screening (such as medium or high throughput drug screening), and for studying molecular pathways involved in glomerular diseases. The disclosure also provides methods for analyzing the healthiness of podocytes in a cell culture. The disclosure also relates to diagnosis of kidney diseases.

21 Claims, 9 Drawing Sheets

Assay method 1- 33 degree proliferation stage
↓
2- partial differentiation in flasks 37 degrees (0-7 days)
↓
3- reseed to plates
↓
4- final differentiation in 37 degree plates (7-14 days)
↓
5- cell treatment
↓
6- cell fixation
↓
7- image acquisition
↓
8- image analysis

(52) U.S. Cl.
CPC ..... *G01N 33/5023* (2013.01); *G01N 33/5026* (2013.01); *G01N 33/5044* (2013.01); *G01N 33/56966* (2013.01); *C12N 2510/04* (2013.01); *G01N 2333/4712* (2013.01); *G01N 2800/347* (2013.01)

(58) Field of Classification Search
CPC ......... G01N 33/56966; G01N 33/5044; G01N 2333/4712
See application file for complete search history.

(56) References Cited

U.S. PATENT DOCUMENTS

| | | |
|---|---|---|
| 2012/0195876 A1 | 8/2012 | Reiser |
| 2012/0251527 A1 | 10/2012 | Reiser |
| 2014/0302065 A1 | 10/2014 | Fomoni et al. |

FOREIGN PATENT DOCUMENTS

| | | |
|---|---|---|
| WO | 2012/054321 A2 | 4/2012 |
| WO | WO 2014/150178 A1 | 9/2014 |

OTHER PUBLICATIONS

R. Ian Freshney, "Subculture and Cell Lines." In: Culture of Animal Cell: A Manual of Basic Technique and Specialized Applications. (Hoboken, NJ, John Wiley & Sons, Inc., 2010), pp. 187-206. QH585.2.F74 2010. (Year: 2010).*
International Search Report dated Jun. 6, 2014 from corresponding PCT Application No. PC/US2014/22497.
Babayeva et al., "Planar Cell Polarity Pathway Regulates Actin Rearrangement, Cell Shape, Motility, and Nephrin Distribution in Podocytes," Am. J. Physiol. Renal Physiol., 300:F549-F560 (2011).
Boguslavsky et al., "p120 Catenin Regulates Lamellipodial Dynamics and Cell Adhesion in Cooperation with Cortactin," PNAS, 104:10882-10887 (2007).
Endlich et al., "Podocytes Respond to Mechanical Stress in Vitro," J. Am. Soc. Nephrol., 12:413-422 (2001).
Fassler et al., "Studying Kidney Injury Using the Operetta System: Analysis of the Podocyte Cytoskeleton on CYTOO Micropatterns," PerkinElmer Application Note, 5 pages (2013).
Ni Lan et al, "Podocyte Culture: Tricks of the Trade", Nephrology, 2012, vol. 17, No. 6, pp. 525-531.
Nazanin Kabgani et al, "Primary Cultures of Glomerular Parietal Epithelial Cells or Podocytes with Proven Origin", PLoS One, 2012, vol. 7, No. 4, p. e34907.
Supplementary European Search Report dated Jul. 8, 2016 from corresponding European Application No. EP 14769052.3.
Alfano et al.; "Full-length soluble urokinase plasminogen activator receptor down-modulates nephrin expression in podocytes"; Scientific Reports, vol. 5; Sep. 2015; p. 13647.
Basu et al.; "Evaluation of Role of G-CSF in the Production, Survival, and Release of Neutrophils from Bone Marrow into Circulation"; Blood 100, vol. 100, No. 3; Aug. 1, 2002; pp. 854-861.
Blasi et al.; "uPAR: A Versatile Signaling Orchestrator"; Nature Reviews / Molecular Cell Biology, vol. 3; Dec. 2002; pp. 932-943.
Brehm et al.; "Humanized mouse models to study human diseases"; Current Opinion in Endocrinology, Diabetes, and Obesity, vol. 17; Apr. 2010; pp. 120-125.
Cathelin et al.; "Administration of recombinant soluble urokinase receptor per se is not sufficient to induce podocyte alterations and proteinuria in mice"; Journal of the American Society of Nephrology, vol. 25; Aug. 2014; pp. 1662-1668.
Cravedi et al.; "Recent Progress in the Pathophysiology and Treatment of FSGS Recurrence"; The American Journal of Transplantation, vol. 13; Feb. 2013; pp. 266-274.
D'Agati et al.; "Focal Segmental Glomerulosclerosis"; The New England Journal of Medicine, vol. 365, No. 25; Dec. 22, 2011; pp. 2398-2411.

Dekkers et al.; "Upregulation of Monocyte Urokinase Plasminogen Activator Receptor during Human Endotoxemia"; Infection and Immunity, vol. 68; Apr. 2000; pp. 2156-2160.
Duran-Struuck et al.; "Principles of Bone Marrow Transplantation (BMT): Providing Optimal Veterinary and Husbanry Care to Irradiated Mice in BMT Studies"; Journal of the American Associateion for Laboratory Animal Science, vol. 48, No. 1; Jan. 2009; pp. 11-22.
Fogo; "Mechanisms of progression of chronic kidney disease"; Pediatric Nephrology, vol. 22; Dec. 2007; pp. 2011-2022.
Gallon et al.; "Resolution of Recurrent Focal Segmental Glomerulosclerosis after Retransplantation"; The New England Journal of Medicine, vol. 366, No. 17; Apr. 26, 2012 pp. 1648-1649.
Hayek et al.; "Soluble Urokinase Receptor and Chronic Kidney Disease"; New England Journal of Medicine, vol. 373; Nov. 12, 2015; pp. 1916-1925.
Holmes et al.; "Concise review: stem cell antigen-1: expression, function, and enigma"; Stem Cells, vol. 25; Jun. 2007; pp. 1339-1347.
Hudkins et al.; "BTBR Ob/Ob mutant mice model progressive diabetic nephropathy"; The Journal of the American Society of Nephrology, vol. 21; Jul. 2010; pp. 1533-1542.
Ito et al.; Current advances in humanized mouse models. Cellular and Molecular Immunology, vol. 9; May 2012; pp. 208-214.
Kistler et al.; "Transient receptor potential channel 6 (TRPC6) protects podocytes during complement-mediated glomerular disease"; Journal of Biological Chemistry, vol. 288; Nov. 2013; pp. 36598-36609.
Kopp et al.; "Transgenic Mice with Increased Plasma Levels of TGF-$\beta$1 Develop Progressive Renal Disease"; Laboratory Investigation, vol. 74, No. 6; Jun. 1996; pp. 991-1003.
Liu et al.; "Impaired production and increased apoptosis of neutrophils in granulocyte colony-stimulating factor receptor-deficient mice"; Immunity, vol. 5; Nov. 1, 1996; pp. 491-501.
Nishimura et al.' "Focal Segmental Glomerular Sclerosis, a Type of Intractable Chronic Glomerulonephritis, Is a Stem Cell Disorder"; Journal of Experimental Medicine, vol. 179; Mar. 1, 1994; pp. 1053-1058.
Papeta et al.; "Prkdc participates in mitochondrial genome maintenance and prevents Adriamycin-induced nephropathy in mice"; The Journal of Clinical Investigation, vol. 120; Nov. 1, 2010; pp. 4055-4064.
Pliyev; "Activated human neutrophils rapidly release the chemotactically active D2D3 form of the urokinase-type plasminogen activator receptor (uPAR/CD87)"; Molecular and Cellular Biochemistry, vol. 321, Jan. 2009; pp. 111-122.
Pliyev et al.; "Release of the Soluble Urokinase-Type Plasminogen Activator Receptor (suPAR) by Activated Neutrophils in Rheumatoid Arthritis"; Inflammation, vol. 33, No. 1; Feb. 2010; 9 pages.
Schiffer et al.; Apoptosis in podocytes induced by TGF-beta and Smad7; The Journal of Clinical Investigation, vol. 108; Sep. 15, 2001; pp. 807-816.
Selleri et al.; "Involvement of the urokinase-type plasminogen activator receptor in hematopoietic stem cell mobilization"; Blood, vol. 105; Mar. 1, 2005; pp. 2198-2205.
Sellier-Leclerc et al.; "A humanized mouse model of idiopathic nephrotic syndrome suggests a pathogenic role for immature cells"; Journal of the American Society of Nephrology, vol. 18; Oct. 1, 2007; pp. 2732-2739.
Shalhoub; "Pathogenesis of Lipoid Nephrosis: A Disorder of T-Cell Function"; The Lancet, vol. 2; Sep. 7, 1974; pp. 556-560.
Shultz et al.; "Human Lymphoid and Myeloid Cell Development in NOD/LtSz-scid IL2R$\gamma^{null}$ Mice Engrafted with Mobilized Human Hemopoietic Stem Cells"; The Journal of Immunology, vol. 174; May 15, 2005; pp. 6477-6489.
Smith et al.; "Regulation of cell signaling by uPAR"; Nature Reviews / Molecular Cell Biology, vol. 11; Jan. 2010; pp. 23-36.
Spinale et al.; "A reassessment of soluble urokinase-type plasminogen activator receptor in glomerular disease"; Kidney International, vol. 87; Mar. 1, 2015; pp. 564-574.
Thunø et al.; "suPAR: The molecular crystal ball"; Disease Markers, vol. 27; 2009; pp. 157-172.

(56) References Cited

OTHER PUBLICATIONS

Tjwa et al.; "Membrane-anchored uPAR regulates the proliferation, marrow pool size, engraftment, and mobilization of mouse hematopoietic stem/progenitor cells"; The Journal of Clinical Investigation, vol. 119; Apr. 2009; pp. 1008-1018.

Wang et al.; "Progressive adriamycin nephropathy in mice: sequence of histologic and immunohistochemical events"; Kidney International, vol. 58; Oct. 2000; pp. 1797-1804.

Wei et al.; "Circulating urokinase receptor as a cause of focal segmental glomerulosclerosis"; Nature Medicine, vol. 17; Aug. 2011; pp. 952-960.

Wei et al.; "Modification of kidney barrier function by the urokinase receptor"; Nature Medicine, vol. 14; Jan. 2008; pp. 55-63.

Winn et al.; "A Mutation in the TRPC6 Cation Channel Causes Familial Focal Segmental Glomerulosclerosis"; Science, vol. 308; Jun. 17, 2005; pp. 1801-1804.

Yu et al.; "Rac1 activation in podocytes induces rapid foot process effacement and proteinuria"; Molecular and Cellular Biology, vol. 33; Sep. 2013; pp. 4755-4764.

Reiser, J. et al. "Toward the Development of Podocyte-Specific Drugs"; Kidney International, vol. 77; Feb. 3, 2010; pp. 662-668.

\* cited by examiner

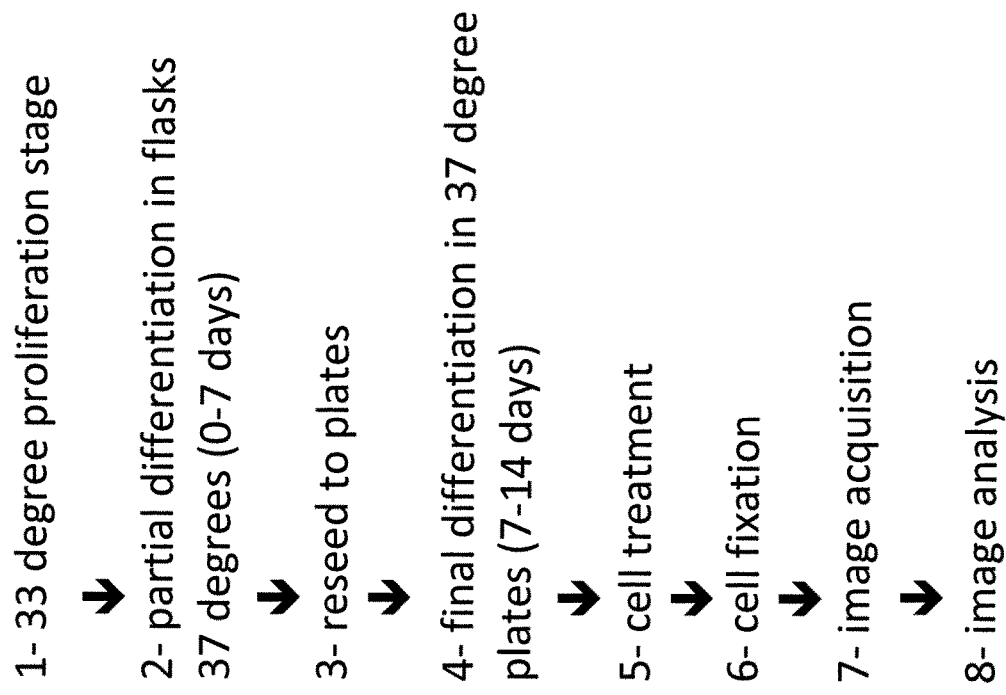

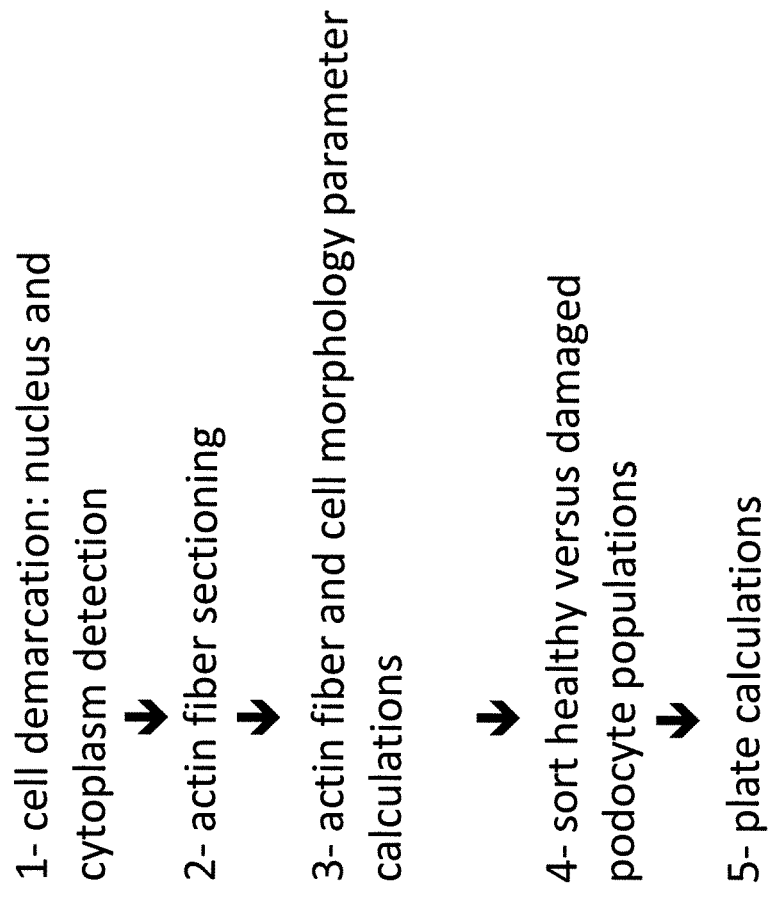
Figure 2: Image analysis method

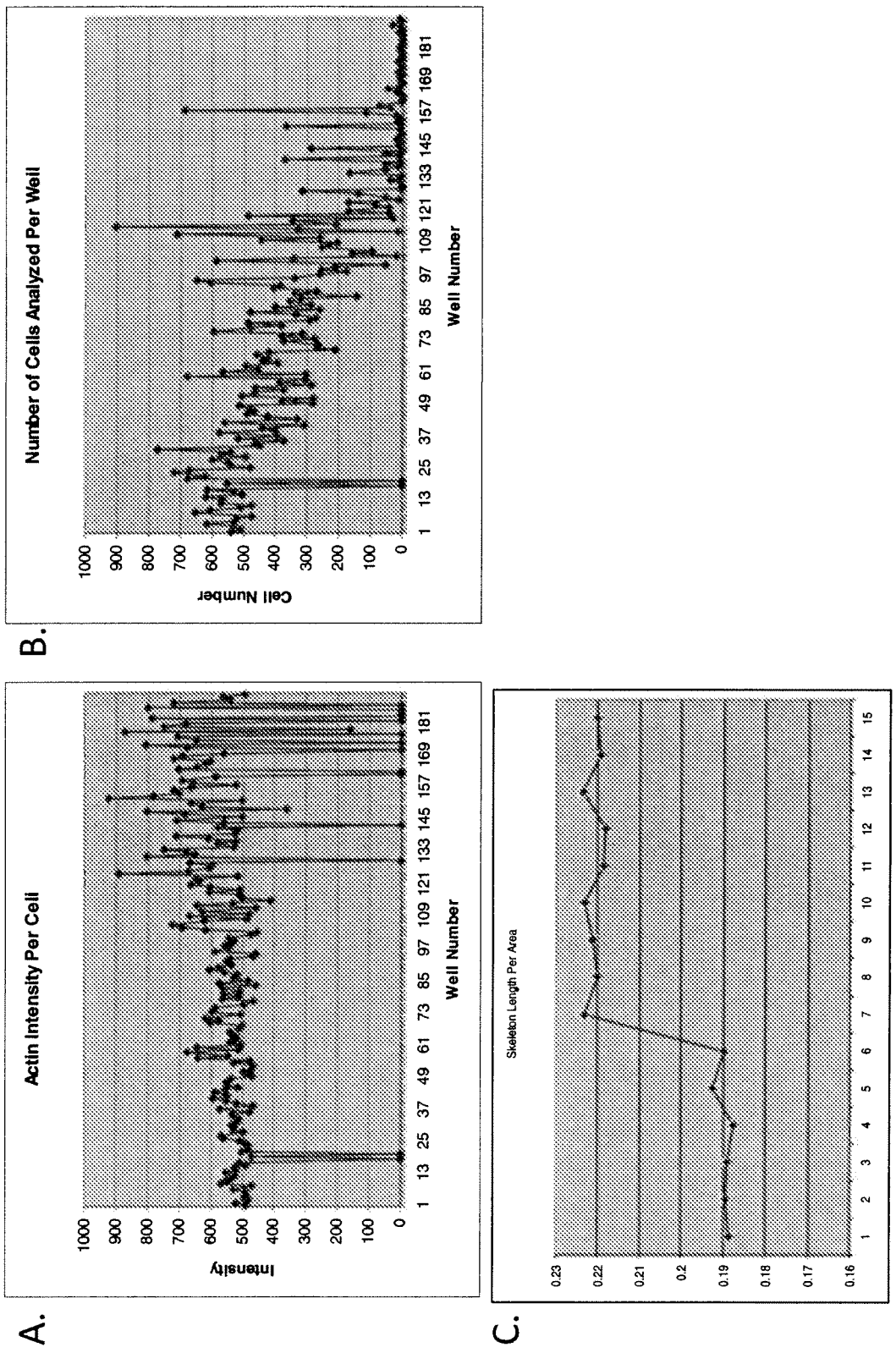
Figure 3: Various parameters for Phenotypic analyses

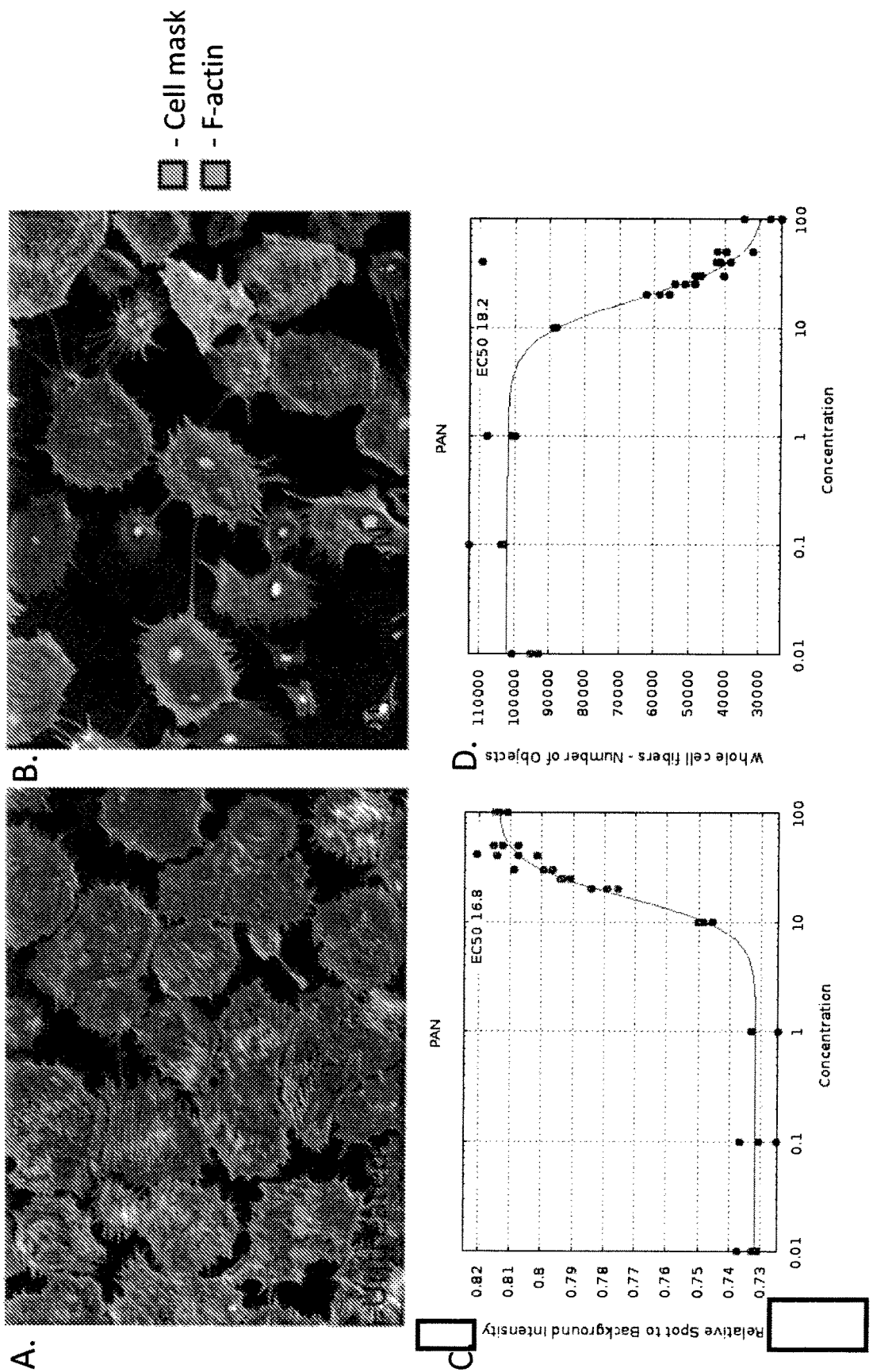

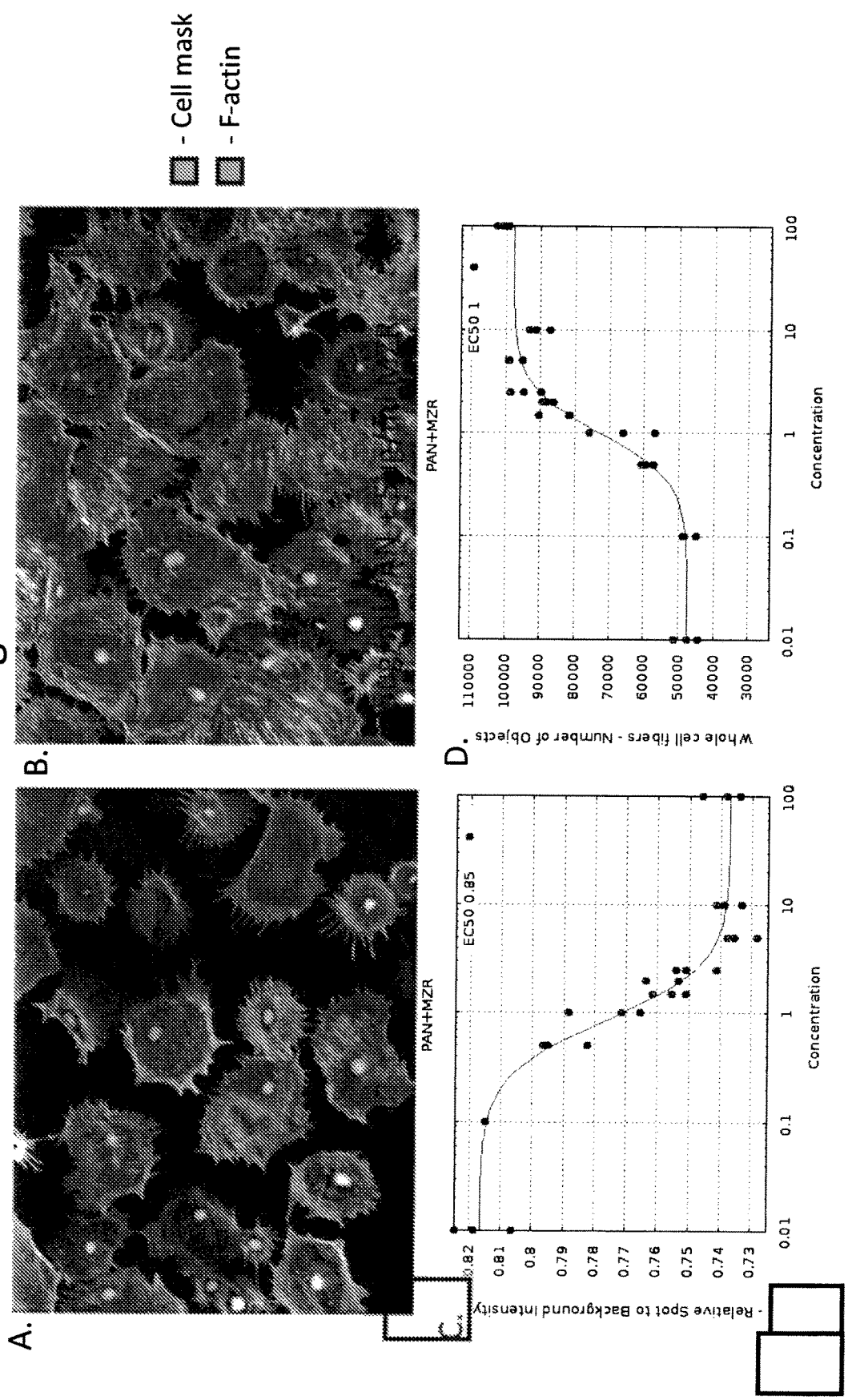
Figure 5: Mizouribine dose-dependently prevents podocyte damage

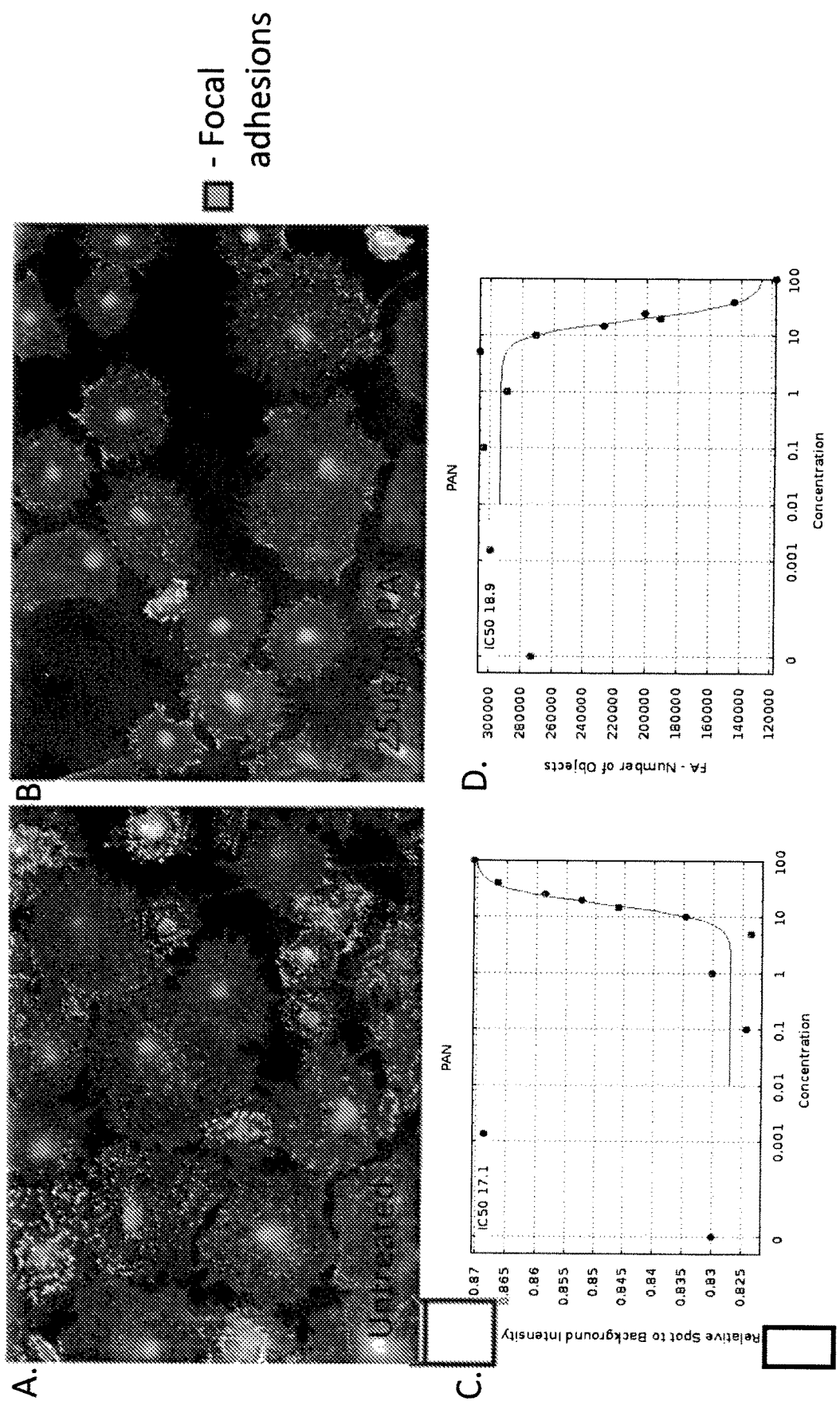
Figure 6: PAN treatment leads to reduced focal adhesions

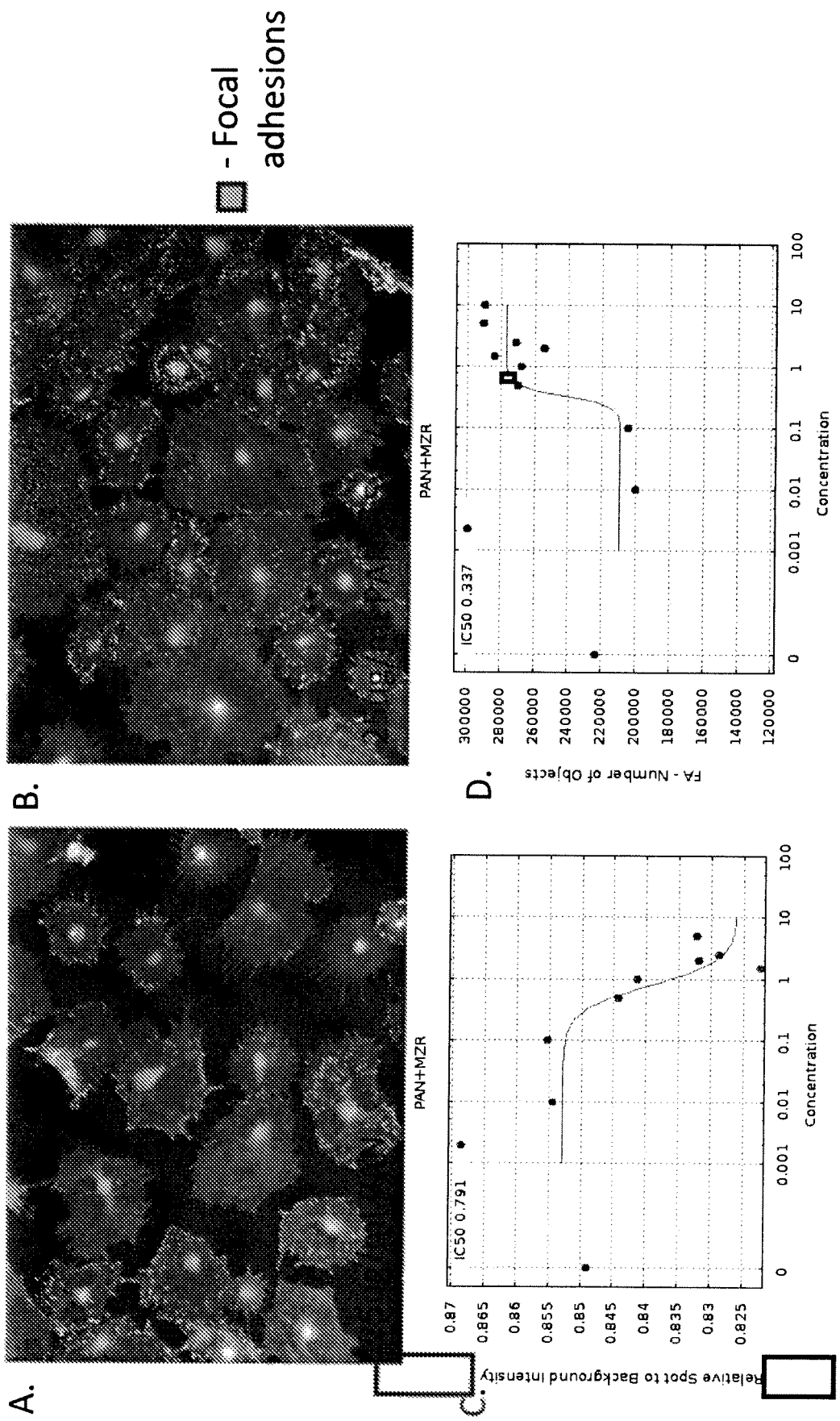
Figure 7: Focal adhesion protection with Mizouribine

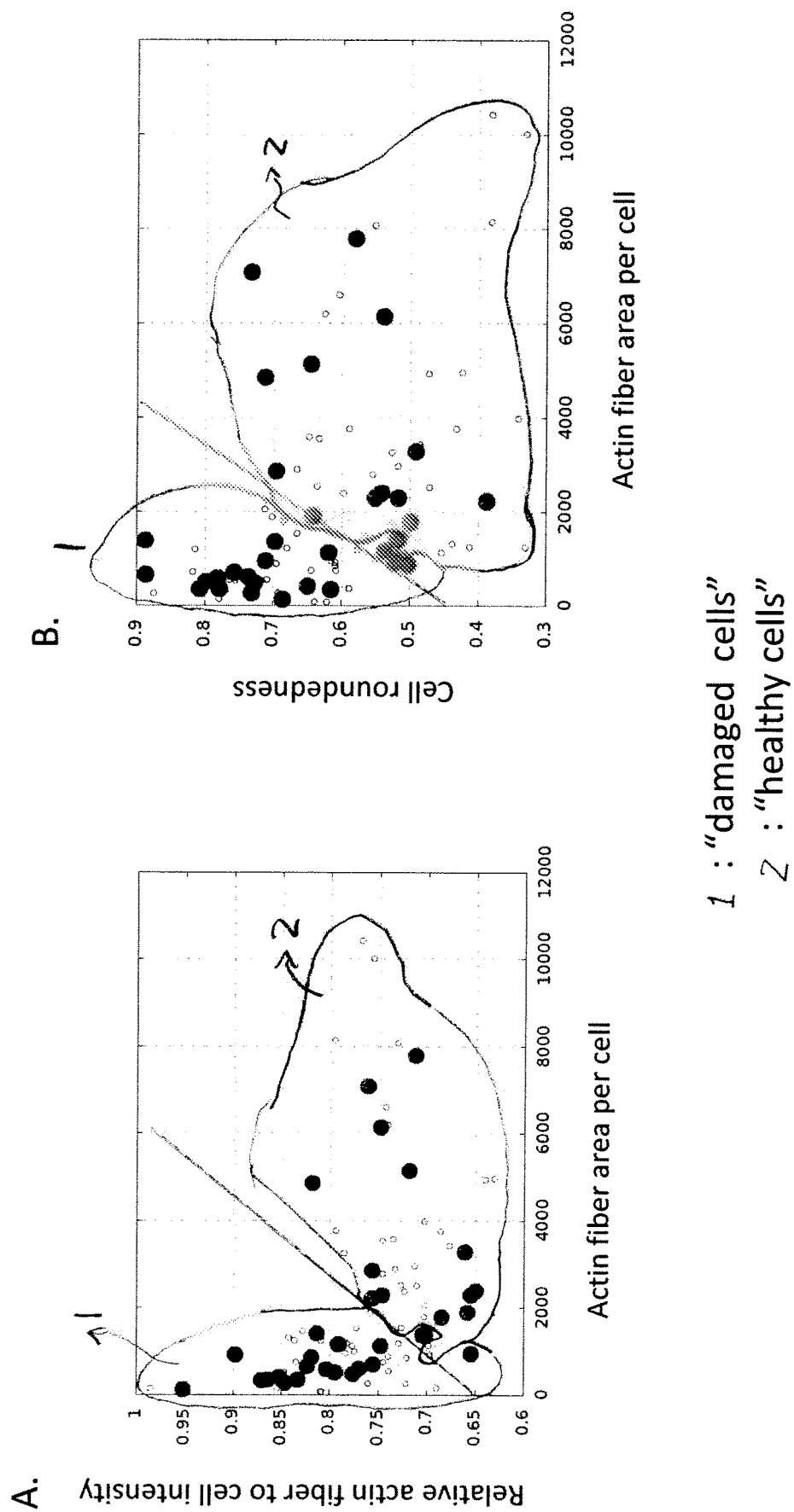
Figure 8: Multiparametric population sorting
1 : "damaged cells"
2 : "healthy cells"

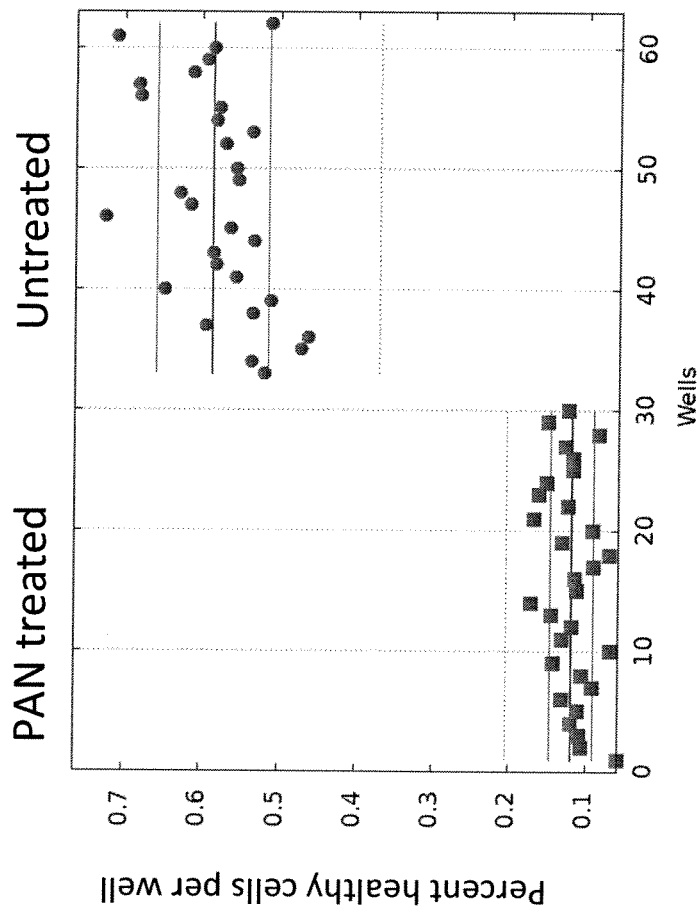
Figure 9: Multiparametric population comparison shows assay robustness

PODOCYTE CULTURES AND USES THEREOF

RELATED APPLICATIONS

This application is the U.S. National Stage of International Application No. PCT/US2014/022497, filed Mar. 10, 2014, published in English, and claims the benefit of U.S. Patent Application No. 61/798,385 filed on Mar. 15, 2013, the entire teachings of which are incorporated herein by reference.

BACKGROUND OF THE INVENTION

Kidney-failure (End stage renal disease, ESRD) is a debilitating disease with no treatments or therapeutics. Patients suffering from ESRD go on dialysis and require a kidney transplant in order to regain kidney function. A majority of kidney diseases and ESRD originate within the glomerulus and are associated with proteinuria. ESRD imposes a significant burden on the patients and the health care system worldwide in is in urgent need for effective therapies and better treatment options.

The study of kidney disease is complex because the onset is often undetected, diseases may be acute or chronic in nature, the genetic makeup of the host leads to variable clinical syndromes, and multiple organs are often involved simultaneously. Cell cultures and animal models are necessary to study disease susceptibility, mechanisms, prognosis, and potential therapies. In renal research, the use of experimental animal models has proved invaluable. Nevertheless, animal models are often limited because they do not always fully replicate the human diseases. For example, the current mouse models of diabetic nephropathy do not typically demonstrate the features of human diseases, such as Kimmelstiel-Wilson nodules.

One of the fastest moving areas of research progress in nephrology has been the appreciation of the importance of the visceral glomerular epithelial cell, hereinafter referred to as the podocyte, in health and disease. Podocytes form the final filtration barrier for blood in the glomerulus and play a central role in glomerular diseases that ultimately result in ESRD (Mundel P. and Reiser J. Kidney Int 2010, 77: 571-80). Podocytes are terminally differentiated pericyte-like cells that reside on the outer surface of the glomerular basement membrane and give rise to long major processes that branch into structures known as foot processes (FPs). FPs of adjacent podocyte cells interdigitate and form narrow filtration slits, a structure known as the slit diaphragm (SD), which forms a molecular sieve that the body uses to retain proteins in the blood, while filtering small molecules and other agents in to the urinary space. Thus, podocyte injury is a common theme in many proteinuric kidney diseases (Mundel P. and Reiser J. Kidney Int 2010, 77: 571-80). Additionally, because of this central role of podocytes in maintaining healthy kidney function, podocytes represent a key target for the development of novel therapeutics to treat a variety of kidney diseases.

Because podocytes play a key role in the prevention of proteinuria in the healthy situation, they are important targets of injury in a variety of renal diseases and are important determinants of outcome. Improved understanding of podocyte biology has come from two main arenas: first, molecular genetics of single gene disorders which lead to rare forms of congenital nephrotic syndrome; and second, focused study of this specialized cell type in vivo and in vitro. Research has also shed light on specific proteins, RNA and cell signaling mechanisms in the podocytes that represent good targets for drug discovery efforts, diagnostics and therapeutics. For example, recent studies have shown that stabilization of the podocyte actin cyctoskeleton, both in vitro and in vivo, can significantly protect the podocytes and ameliorate proteinuria in vivo, suggesting that such agents may have a therapeutic potential for treating proteinuria in humans.

Although podocyte cultures do not fully replicate the in vivo environment, they have several major advantages. These include the ability to directly study mechanistic events, to control the environment such that specific hypotheses can be tested, and that multiple experiments can be performed to validate the initial observations.

Currently, a significant limitation in using podocyte cultures is the difficulty in handling podocytes and using them in a medium- or high-throughput assay environment (Reiser, Gupta et al, Kidney Int. (2010) 77, 662). Assays for systematic, high-throughput screening of libraries of potential agents are not available. Podocytes are a challenging cell type for use in such assays.

A need exists for developing podocyte cultures that are suitable for drug screening (such as high throughput drug screening), and for studying molecular pathways involved in glomerular diseases.

SUMMARY OF THE INVENTION

The invention generally relates to methods of culturing podocytes in vitro. The method comprises maintaining a first culture of podocyte cells (e.g., primary podocytes or podocyte cell lines, such as conditionally-immortalized podocyte cell lines) under a permissive condition or proliferation condition to produce a population of podocytes, maintaining that population of podocytes (or a fraction thereof) under a non-permissive condition or differentiation condition for a period of time sufficient to obtain a population of partially differentiated podocytes, and then maintaining the partially differentiated podocytes (or a fraction thereof) in a second culture under a non-permissive condition or differentiation condition for a period of time sufficient to obtain a population of terminally-differentiated podocytes.

The cultures and terminally-differentiated podocytes obtained from the cultures can be used for a variety of purposes, such as drug screening (such as medium or high throughput drug screening), studying molecular pathways involved in glomerular diseases, and diagnosing and screening patients for kidney disease or predisposition for kidney disease. The invention also provides methods for analyzing the healthiness of podocytes.

BRIEF DESCRIPTION OF THE DRAWINGS

FIG. 1 is a flow chart describing an exemplary phenotypic podocyte assays used in medium- to high-throughput, high-content screening (HCS). Cultured podocytes can be used in HCS assays for automated detection of cellular changes in a medium- to high-throughput environment. In this method, podocytes are partially differentiated in culture flasks and subsequently transferred to multi-well assay plates, followed by additional differentiation time. Cells are then used in downstream assays to obtain a highly robust, reproducible and low-variable cellular phenotype.

FIG. 2 is a flow chart describing an exemplary method for phenotypic podocyte assays used in medium- to high-throughput, high-content screening (HCS). Podocytes in multi-well plates are analyzed using high content screening imagers. The images are then analyzed. Under this approach, one important step is the identification of parameters for differentiating between healthy and injured or diseased podocytes. Using multiple parameters to differentiate between healthy podocytes from damaged or diseased podocytes also provided a robust analysis method.

FIG. 3 shows various parameters that are useful in phenotypic analyses of podocytes. A-B. Graphs showing a variety of analyses that were applied to healthy podocytes cultured in 384-well multiwell plates. Different number of cells were plated in different wells of the plate and analyzed to also study the effects of cell number. A. A graph showing normalized (on a per cell basis) intensity of F-actin in wells containing decreasing number of podocytes per well (highest in well #1, approximately 500 cells were analyzed in that well), as determined using an F-actin fluorescent stain (fluorescently labeled phalloidin). It clearly shows that normalized F-actin intensity can be used as a quantitative feature for cellular analysis, as long as the cell number is higher than about 100-200, when the data shows much higher variability. B. A graph showing number of podocytes per well (highest in well #1, approximately 500 cells were analyzed in that well), as determined using a fluorescent nuclear stain. It shows a linear correlation with cell number in the wells of 384-well plate between 500 and 100 analyzed cells/wells below which the data shows much higher variability. C. Graph showing measurement of a parameter, average length of actin cytoskeleton per image area, and shows significant convergence for features in healthy cells versus damaged cells. Healthy cells show longer skeletal length (approx. 0.22) versus the damaged cells (approx. 0.19).

FIG. 4 shows PAN dose-response curve. A dose-response curve showing the effects of increasing concentration of podocyte injuring drug puromycin aminonucleoside (PAN) on various cellular parameters, including the intensity and the number of actin fibers, in cultured podocytes. Differentiated podocytes were cultured in 96-well multiwell plates. Cells were either kept in normal cell culture media or were treated with increasing concentration of PAN for 48 h at 37° C. Subsequently, the cells were fixed with paraformaldehyde and the filamentous actin (F-actin) fibers stained using Alexa Fluor 594-labeled phalloidin. Cells were imaged using PerkinElmer OPERA High-content screening microscope and the images were analyzed using PerkinElmer Columbus analysis system to count F-actin fibers per cell in each well of the multiwell plate. FIGS. 4A and 4B show representative images of untreated (A) and PAN-treated (B) podocytes. FIG. 4C shows a graph of the parameter "relative spot to background intensity" (a measurement which contrasts the intensity of sectioned F-actin fibers in a ratio to the intensity of the cell on a per cell basis and computed for the average for the well) versus PAN concentration. FIG. 4D shows a graph of the parameter "Whole cell fibers—number of objects" (which counts the number of sectioned F-actin fibers per well based on a threshold) versus PAN concentration. The method allowed quantitative assessment of podocyte damage in a dose-response fashion using these parameters based on the podocyte actin cytoskeleton when treated with the compound puromycin aminonucleoside or PAN. These two parameters also gave a reproducible IC50 value for PAN as an in vitro podocyte damaging agent. Each data point represents average F-actin fiber count per cell (from approximately 500-2000 cells/well) from a single well.

FIG. 5. Mizouribine dose-dependently prevents podocyte damage. Dose-response curves showing the effects of co-treatment of PAN and podocyte-protective drug mizouribine on various cellular parameters, including the intensity and the number of actin fibers, in cultured podocytes. Differentiated podocytes were cultured in 96-well multiwell plates. Cells were treated with PAN in the absence or presence of increasing concentration of mizouribine for 48 h at 37° C. Subsequently, the cells were fixed with paraformaldehyde and the filamentous actin (F-actin) fibers stained using Alexa Fluor 594-labeled phalloidin. Cells were imaged using PerkinElmer OPERA High-content screening microscope and the images were analyzed using PerkinElmer Columbus analysis system to count F-actin fibers per cell in each well of the multiwell plate. FIGS. 5A and 5B show representative images of PAN damaged podocytes (A) and PAN and Mizouribine co-treated healthy podocytes (B), which show that Mizouribine protects podocytes and protects the actin fibers from PAN damage. FIG. 5C shows a graph of the parameter "relative spot to background intensity" (a measurement which contrasts the intensity of sectioned F-actin fibers in a ratio to the intensity of the cell on a per cell basis and computed for the average for the well) versus mizouribine concentration. FIG. 5D shows a graph of the parameter "Whole cell fibers—number of objects" (which counts the number of sectioned F-actin fibers per well based on a threshold) versus mizouribine concentration. The method allowed quantitative assessment of protection of podocyte damage in a dose-response fashion using these parameters based on the podocyte actin cytoskeleton when treated with PAN and mizouribine. These two parameters also gave a reproducible IC50 value for mizouribine as an in vitro podocyte protective agent. Each data point represents average F-actin fiber count per cell (from approximately 500-2000 cells/well) from a single well.

FIG. 6. PAN treatment leads to reduced focal adhesions. Here, a dose-response curve shows the effects of increasing concentrations of podocyte injuring drug puromycin aminonucleoside (PAN) on the number and intensity of focal adhesions as a cellular parameter for cultured podocytes. Differentiated podocytes were cultured in 96-well multiwell plates. Cells were either kept in normal cell culture media or were treated with increasing concentration of PAN for 48 h at 37° C. Subsequently, the cells were fixed with paraformaldehyde and the focal adhesions were stained using an anti-paxillin antibody. Cells were imaged using PerkinElmer OPERA High-content screening microscope and the images were analyzed using PerkinElmer Columbus analysis system to count F-actin fibers per cell in each well of the multiwell plate. FIGS. 6A and 6B show representative images of untreated (A) and PAN-treated (B) podocytes. FIG. 6C shows a graph of the parameter "relative spot to background intensity" (a measurement which contrasts the intensity of the sectioned focal adhesion in a ratio to the intensity of the cell on a per cell basis and the computed average for the well) versus PAN concentration. FIG. 6D shows a graph of the parameter "FA—number of objects" (which counts the number of sectioned focal adhesions per well based on a threshold) versus PAN concentration. The method allowed quantitative assessment of podocyte damage in a dose-response fashion using these parameters based on the podocyte focal adhesions when treated with the compound puromycin aminonucleoside or PAN. These two parameters also gave a reproducible IC50 value for PAN as an in vitro podocyte damaging agent. Each data point represents average count per cell (from approximately 500-2000 cells/well) from a single well.

FIG. 7. Focal adhesion protection with Mizouribine. Mizouribine dose-dependently prevents podocyte damage.

Dose-response curves showing the effects of co-treatment of PAN and podocyte-protective drug mizouribine on various cellular parameters, including the number of focal adhesions, in cultured podocytes. Differentiated podocytes were cultured in 96-well multiwell plates. Cells were treated with PAN in the absence or presence of increasing concentration of mizouribine for 48 h at 37° C. Subsequently, the cells were fixed with paraformaldehyde and the focal adhesions were stained using fluorescently labeled paxillin. Cells were imaged using PerkinElmer OPERA High-content screening microscope and the images were analyzed using PerkinElmer Columbus analysis system to count F-actin fibers per cell in each well of the multiwell plate. FIGS. 7A and 7B show representative images of PAN damaged podocytes (A) and PAN and Mizouribine co-treated healthy podocytes (B), which show that Mizouribine protects podocytes and protects the focal adhesions from PAN damage. FIG. 7C shows a graph of the parameter shows a graph of the parameter "relative spot to background intensity" (a measurement which contrasts the intensity of the sectioned focal adhesion in a ratio to the intensity of the cell on a per cell basis and the computed average for the well) versus mizouribine concentration. FIG. 7D shows a graph of the parameter "FA—number of objects" (which counts the number of sectioned focal adhesions per well based on a threshold) versus mizouribine concentration. The method allowed quantitative assessment of podocyte protection in a dose-response fashion using these parameters based on the podocyte focal adhesions when treated with the compounds PAN and mizouribine. These two parameters also gave a reproducible IC50 value for mizouribine as an in vitro podocyte protecting agent. Each data point represents average count per cell (from approximately 500-2000 cells/well) from a single well.

FIG. 8. Multiparametric population sorting. The results presented here show that combining multiple analysis parameters can further improve the quantitative differences between healthy and damaged podocytes. Differentiated podocytes were cultured in 96-well multiwell plates. Cells were either kept in normal cell culture media or were treated with a single concentration of PAN (20 ug/mL) for 48 h at 37° C. Subsequently, the cells were fixed with paraformaldehyde and the filamentous actin (F-actin) fibers stained using Alexa Fluor 594-labeled phalloidin. Cells were imaged using PerkinElmer OPERA High-content screening microscope and the images were analyzed using PerkinElmer Columbus analysis system to count F-actin fibers per cell in each well of the multiwell plate. Cell morphology was also analyzed. FIGS. 8A and 8B show 2 examples of parameters that were usee to sort populations of cells. In both figures, the dotted line represents the cutoff between the populations of healthy (green dots) and damaged (represented by red dots) podocytes to create the best separation between groups and can be used to bin the populations of cells for subsequent plate calculations.

FIG. 9. Multiparametric population comparison shows assay robustness. The results presented here show that combining multiple analysis parameters can further improve the quantitative differences between healthy and damaged podocytes and provide a robust, reproducible and low-variable assay that is highly applicable in a medium- to high-throughput assay environment. Differentiated podocytes were cultured in 96-well multiwell plates. Cells were either kept in normal cell culture media or were treated with a single concentration of PAN (20 ug/mL) for 48 h at 37° C. Subsequently, the cells were fixed with paraformaldehyde and the filamentous actin (F-actin) fibers stained using Alexa Fluor 594-labeled phalloidin. Cells were images using PerkinElmer OPERA High-content screening microscope and the images were analyzed using PerkinElmer Columbus analysis system to count F-actin fibers per cell in each well of the multiwell plate. Cell morphology was also analyzed. In the presented graph, shows the results of a test of the assays robustness using multiparametric population sorting with a group of PAN damaged cells versus untreated based on the percentage of healthy podocytes in the well. There was a clear separation between the quantitative number for healthy cells and that for damaged cells. Data are mean±1 SD (darker set of lines) and mean±3 SD (lighter lines) at each point.

DETAILED DESCRIPTION OF THE INVENTION

1. Overview

The invention generally relates to methods of culturing podocytes in vitro. The method comprises maintaining a first culture of podocyte cells (e.g., primary podocytes, proliferating podocytes, podocyte precursor cells or podocyte cell lines, such as conditionally-immortalized podocyte cell lines) under a permissive condition or proliferation condition to produce a population of podocytes, maintaining that population of podocytes (or a fraction thereof) under a non-permissive condition or differentiation condition for a period of time sufficient to obtain a population of partially differentiated podocytes, and then maintaining the partially differentiated podocytes (or a fraction thereof) in a second culture under a non-permissive condition or differentiation condition for a period of time sufficient to obtain a population of terminally-differentiated podocytes.

The cultures and terminally-differentiated podocytes obtained from the cultures can be used for a variety of purposes, such as drug screening (such as medium or high throughput drug screening), studying molecular pathways involved in glomerular diseases, and diagnosing and screening patients for kidney disease or predisposition for kidney disease.

The invention also provides methods for analyzing the healthiness of podocytes.

A significant limitation in using podocyte cultures is the difficulty in handling podocytes and using them in medium- or high-throughput assays. Podocytes show heterogeneous morphology in in vitro cultures, which makes it hard to get robust, reproducible data with low-variability between different wells, plates, and on different days. The numbers of podocyte cells per well are also highly variable from well-to-well and plate-to-plate, because of the long culture time needed for the proliferation and differentiate these cells in vitro. Additionally, differentiated podocytes have shown limited ability to propagate.

As described and exemplified herein, the inventors have developed new methods of culturing podocytes in vitro, which produce podocyte cultures that are suitable for, among other purposes, medium- or high-throughput assays. For example, as exemplified in FIG. 1, first, conditionally-immortalized podocytes were proliferated under a permissive condition to achieve a desired number of cells (in this example, 100% confluency). Second, the cells were maintained under a non-permissive condition to induce partial differentiation. Third, these partially differentiated cells were re-seeded in a multi-well plate, in which the partially differentiated cells were maintained under a non-permissive condition to produce terminally-differentiated podocytes.

Using this method, robust, reproducible and homogenous podocyte cultures in the multiwell format were achieved. The method also significantly improves the quality of the podocytes, so that the well-to-well and plate-to-plate variability is low. Podocytes produced by this method are particularly suitable for use in medium- and high-throughput assays (such as drug screenings).

As described and exemplified herein, the inventors also developed assays and methods to analyze cellular and physiological characteristics of terminally differentiated podocytes, such as membrane permeability, morphology, viability, or expression of a podocyte marker. For example, image analysis algorithms were developed to determine podocyte health using specific measurements of the actin cytoskeleton, focal adhesions, and morphology of the podocyte in vitro. In one example, the methods were used to quantify changes in podocytes caused by a damaging agent, or a damaging agent together with an agent to maintain or improve podocyte health. In another example, the inventors quantified the changes in podocytes using multiple parameters to segregate different population subtypes in a single well.

2. Definitions

As used herein, the singular forms "a," "an" and "the" include plural references unless the content clearly dictates otherwise.

The term "about", as used here, refers to +/−10% of a value.

A "conditionally-immortalized" podocyte refers to an immortalized podocyte in which the mitotic proliferation of the podocyte can be activated or inactivated under appropriate conditions. Under a "permissive condition," the cell proceeds with mitotic proliferation, and under a "non-permissive condition," the cell proceeds to differentiate. A conditionally immortalized podocyte line can be constructed in a number of ways. For example, a foreign gene encoding a temperature-sensitive immortalizing molecule, such as the polyoma-large T antigen, can be integrated in the genome of a cell. The resulting cell line can be grown at temperatures at which the immortalizing molecule is active, or at which the molecule becomes inactive, such as between about 30° C. and 40° C.

Conditionally immortalized human podocyte cell lines have been developed by transfection using both the temperature-sensitive mutant $U19_{ts}A58$ of the SV40 large T antigen (SV40) and the essential catalytic subunit of the hTERT telomerase gene. The hTERT vector expresses telomerase activity to maintain telomere length, preventing the occurrence of replicative senescence. Transfection of cells with SV40T allows cells to proliferate at the "permissive" temperature of 33° C. Transfer to the "non-permissive" temperature of 37° C. results in the inactivation of large T antigen with minor changes in gene expression. Podocytes then enter growth arrest and express markers of differentiated in vivo podocytes, including the podocyte proteins, nephrin, podocin, CD2AP, and synaptopodin, and known molecules of the slit diaphragm ZO-1, alpha-, beta-, and gamma-catenin and P-cadherin. See, e.g., Ni et al., Podocyte culture: Tricks of the trade, Nephrology 17 (2012) 525-531.

As used herein, the term "permissive condition" refers to a cell culture condition that allows a podocyte to divide and propagate, without inducing apparent terminal differentiation. For example, a conditionally immortalized murine podocyte cell line (Mundel, Reiser et al., Experimental Cell Research, 236, p 248 (1997)) can be propagated at 33 degree centigrade and media containing 10 U/ml recombinant mouse γ-interferon (permissive condition).

As used herein, the term "non-permissive condition" refers to a cell culture condition that induces terminal differentiation of a podocyte, which may be demonstrated, for example, by the expression of makers that are typically expressed in fully differentiated podocytes in the kidney. For example, a conditionally immortalized murine podocyte cell line (Mundel, Reiser et al., Experimental Cell Research, 236, p 248 (1997)) can be differentiated by shifting the cells from 33 degree centigrade to a 37 degree centigrade cell culture environment and excluding recombinant mouse γ-interferon from the media (non-permissive condition).

A "terminally differentiated" podocyte refers to a cell that typically doesn't enter mitotic cell cycle and is further characterized by its arborized appearance, large cell size, an organized actin cytoskeleton, and podocyte specific markers. The following proteins have been identified as being markers for a terminally differentiated podocyte: $\alpha 3\beta 1$ integrin, α-Actinin-4, CD2AP, Nephrin, Podocalyxin, Podocin, Synaptopodin, VEGF, WT-1. See, e.g., Shankland et al., Podocytes in culture: past, present, and future, *Kidney International* (2007) 72, 26-36; doi:10.1038/sj.ki.5002291; and Pavenstadt et al., Cell Biology of the Glomerular Podocyte, Physil. Rev., (2003) 83, 253-307; doi: 10.1152/physrev.00020.2002

A "partially differentiated" podocyte refers to a cell that has differentiated from a conditionally-immortalized podocyte, a proliferating podocyte or a podocyte precursor cell, but is not terminally differentiated. A partially differentiated podocyte is phenotypically different from a conditionally-immortalized podocyte, a proliferating podocyte, a podocyte precursor cell and a terminally differentiated podocyte, and can be further characterized by only partial expression of differentiated podocyte markers and phenotype. Generally, under a permissive condition, immortalized podocytes show a typical cobblestone morphology. Shifting the cells to a non-permissive condition typically results in arrest of proliferation, enlarging of cell bodies to an irregular shape, and formation of both short and more rounded, as well as long, spindle-like projections, similar to those described for primary podocyte cultures. A "partialy differentiated" podocyte shows partial expression of markers typically present in a "terminally differentiated" podocyte. This includes proteins, such as Synaptopodin and podocin. The level of expression of these proteins in "partially-differentiated" podocytes is less than that of the levels typically present in a "terminally differentiated" podocyte.

A primary cell culture refers to a cell culture in which the cells are isolated directly from an organism or a tissue sample and proliferated under the appropriate conditions, with no passages.

A "proliferation condition" for a podocyte culture refers to a condition that allows a podocyte to divide and propagate, without inducing apparent terminal differentiation. Typically, a primary podocyte remains proliferative when the cell density of the culture is below about 50% confluent (when grown as an adherent culture).

A "differentiation condition" for a podocyte culture refers to a condition that induces terminal differentiation of a podocyte. Typically, a primary podocyte starts differentiation when the cell density of the culture is above about 50% confluent (when grown as an adherent culture).

A terminally differentiated podocyte is "healthy" when the podocyte is viable and has other characteristics of normal podocytes. Typically, healthy podocytes expresses the marker proteins Podocin and Synaptopodin at levels typical of normal terminally differentiated podocytes, which are known in the art.

3. Podocyte Cultures

In one aspect, the invention relates to in vitro podocyte cultures and to the podocytes produced using such cultures. The podocytes can be from any desired animal species, such as a mammal (e.g., murine (mouse, rat), human) or non-mammal, such as fish (e.g., zebra fish) or insect (e.g. *Drosophila*).

In one aspect, the invention provides a method of culturing podocytes in vitro, comprising: (a) maintaining podocyte cells (e.g, primary podocytes, proliferating podocytes, podocyte precursor cells or podocyte cell lines, such as conditionally-immortalized podocyte cell lines) in a first cell culture under a permissive condition or proliferation condition for a period of time sufficient for the conditionally-immortalized podocyte to double at least once, thereby producing a population of podocytes; (b) maintaining the population of podocytes obtained in (a) under a non-permissive condition or differentiation condition for a period of time sufficient to obtain a population of partially differentiated podocytes; and (c) maintaining the partially differentiated podocytes obtained in (b) in a second cell culture under a non-permissive condition or differentiation condition for a period of time sufficient to obtain a population of terminally-differentiated podocytes.

In particular embodiments, the first cell culture contains a primary podocyte, a podocyte precursor, a proliferative podocyte or a podocyte cell line. Typically, a primary podocyte remains proliferative when the cell density of the culture is below about 50% confluent (when grown as an adherent culture), and starts differentiation when the cell density of the culture is above about 50% confluent (when grown as an adherent culture). In more particular embodiments, the first cell culture contains a conditionally-immortalized podocyte cell line.

A number of podocyte cell lines, including wild-type and knockout murine cell lines, as well as wild-type and genetically altered human podocyte lines, are available and can be used in the methods described herein. Table 1 summarizes some of the podocyte cell lines that may be used.

TABLE 1

Exemplary podocyte cell lines

| Podocyte cell line | Refs. |
|---|---|
| Wild-type mouse | Mundel P, Reiser J, Borja AZ et al. Rearrangements of the cytoskeleton and cell contacts induce process formation during differentiation of conditionally immortalized mouse podocyte cell lines. *Exp Cell* Res 1997; 236: 248-258 and Schiwek D, Endlich N, Holzman L et al. Stable expression of nephrin and localization to cell-cell contacts in novel murine podocyte cell lines. *Kidney Int* 2004; 66: 91-101 |
| $\alpha 3$ Integrin$^{-/-}$ | Reiser J, Von Gersdorff G, Loos M et al. Induction of B7-1 in podocytes is associated with nephrotic syndrome. *J Clin Invest* 2004; 113: 1390-1397. |
| CD2AP$^{-/-}$ | Schiffer M, Mundel P, Shaw AS et al. A novel role for the adaptor molecule CD2-associated protein in TGF-beta-induced apoptosis. *J Biol Chem* 2004; 279: 37004-37012 |
| FGF2$^{-/-}$ | Davidson G, Dono R, Zeller R. FGF signalling is required for differentiation-induced cytoskeletal reorganisation and formation of actin-based processes by podocytes. *J Cell Sci* 2001; 114: 3359-3366 |
| Cyclin I$^{-/-}$ | Griffin SV, Olivier JP, Pippin JW et al. Cyclin I protects podocytes from apoptosis. *J Biol Chem* 2006; 281: 28048-28057. |
| p21$^{-/-}$ | Wada T, Pippin JW, Terada Y et al. The cyclin-dependent kinase inhibitor p21 is required for TGF-beta1-induced podocyte apoptosis. *Kidney Int* 2005; 68: 1618-1629 and Petermann AT, Pippin J, Durvasula R et al. Mechanical stretch induces podocyte hypertrophy *in vitro*. *Kidney Int* 2005; 67: 157-166. |
| p27$^{-/-}$ | Petermann AT, Pippin J, Durvasula R et al. Mechanical stretch induces podocyte hypertrophy *in vitro*. *Kidney Int* 2005; 67: 157-166. |
| Synaptopodin$^{-/-}$ | Asanuma K, Kim K, Oh J et al. Synaptopodin regulates the actin-bundling activity of alpha-actinin in an isoform-specific manner. *J Clin Invest* 2005; 115: 1188-1198 |
| HIV transgenic | Schwartz EJ, Cara A, Snoeck H et al. Human immunodeficiency virus-1 induces loss of contact inhibition in podocytes. *J Am Soc Nephrol* 2001; 12: 1677-1684 |
| Wild-type human | Saleem MA, O'Hare MJ, Reiser J et al. A conditionally immortalized human podocyte cell line demonstrating nephrin and podocin expression. *J Am Soc Nephrol* 2002; 13: 630-638 |
| DDS mutant human | Viney RL, Morrison AA, Van den Heuvel LP et al. A proteomic investigation of glomerular podocytes from a Denys-Drash syndrome patient with a mutation in the Wilms tumour suppressor gene WT1. *Proteomics* 2007; 7: 804-815. |

Conditionally immortalized podocyte cell lines are proliferative when cultured under permissive conditions. Non-permissive conditions cause growth arrest in the majority of podocytes within a couple of days and induces many characteristics of differentiated podocytes.

Similar to undifferentiated primary podocytes in culture, actively proliferating conditionally immortalized podocytes growing under permissive conditions display an epithelial morphology. They are small in size, exhibit a polygonal or "cobblestone" appearance, and have a relatively small cytoplasmic volume. When podocytes are placed in non-permissive conditions, again similar to primary differentiated podocytes, they substantially increase in size, stop replicating, and take on a more complex arborized morphology including the formation of cellular structures comparable with filtration slits in vivo. Podocytes are typically plated in non-permissive conditions at a concentration of 5,000-10,000 cells/cm².

In addition to conditionally immortalized podocyte cell lines that are currently available in the art, conditionally immortalized podocyte cell lines may also be made from primary cultures. Methods of isolating podocytes to produce a primary culture, and immortalizing podocytes are known in the art. See, e.g., Ni et al., Podocyte culture: Tricks of the trade, Nephrology 17 (2012) 525-531.

Both proliferating and differentiating podocytes express WT-1. During differentiation, an ordered array of actin fibers and microtubules started to extend into the forming cellular processes, reminiscent of podocyte processes in vivo. Similar to primary cultures, the cytoskeletal rearrangement and process formation were accompanied by the onset of synaptopodin expression. Moreover, electrophysiological studies showed that differentiated murine podocytes respond to bradykinin by changes in intracellular calcium concentration.

Terminally differentiated podocytes typically do not enter mitotic cell cycle and are further characterized by arborized appearance, large cell size, an organized actin cytoskeleton, and podocyte specific markers. Table 2 summarizes certain characteristics of terminally-differentiated podocytes. These characteristics may be used individually or in combination to determine the differentiation state of podocytes.

TABLE 2

Selected criteria for terminally-differentiated podocytes

| Feature | Details |
|---|---|
| Morphology | Arborized appearance |
| | Processes extend from cell body |
| | Large cytoplasmic to nuclear volume ratio |
| | Stress fiber formation |
| Protein expression | WT-1 |
| | Synaptopodin |
| | Nephrin |
| | Podocin |
| | CD2AP |
| | Ezrin |
| | VEGF production |
| Cell cycle | Absence of DNA synthesis (negative for Brdu. PCNA, cyclin E, and A; no cdk2 activity) |
| | Absence of mitosis (negative for cyclin B. no cdc2 activity; no mitotic figures) |
| | Expression of p27 and p57 |
| | Do not require cell-cell contact to exit cell cycle |
| Functional responses | Apoptosis induced by TGF-β, PAN |
| | Motile |
| | Processes induced by ATRA |
| | Dexamethasone induces shape changes and enhanced survival |

ATRA, all-trans retinoic acid;
PAN, puromycin aminonucleoside;
PCNA, proliferating cell nuclear antigen;
TGF, transforming growth factor;
VEGF, vascular endothelial growth factor.

Typically, in step (a), the first podocyte culture is maintained under a permissive condition (e.g., for conditionally-amortized cells) or a proliferation condition (e.g., for primary podocytes, podocyte precursors, or other types proliferative podocytes) for between about 3 days and about 30 days, between about 5 days and about 20 days, or between about 7 days and about 14 days.

The first podocyte culture can be any desired type of culture, such as a suspension culture or an adherent culture. In certain embodiments, the first podocyte culture is an adherent culture. In certain embodiments, the population of podocytes are maintained at least about 50% confluent, at least about 60% confluent, at least about 70% confluent, at least about 80% confluent, or at least about 90% confluent, in an adherent culture before partial differentiation is initiated.

Typically, in step (b), during the partial differentiation stage, the population of podocytes are maintained under a non-permissive condition (e.g., for conditionally-amortized cells) or a differentiation condition (e.g., for primary podocytes, podocyte precursors, or other types proliferative podocytes) for between about 1 days and about 12 days, between about 3 days and about 10 days, between about 4 days and about 8 days, or between about 5 days and about 7 days. The culture can be any desired type of culture, such as a suspension culture or an adherent culture.

Typically, in step (c) during the terminal differentiation stage, the partially differentiated podocytes are maintained under a non-permissive condition (e.g., for conditionally-amortized cells) or a differentiation condition (e.g., for primary podocytes, podocyte precursors, or other types proliferative podocytes) for about 3 days and about 30 days, between about 5 days and about 20 days, or between about 6 days and about 15 days. The culture can be any desired type of culture, such as a suspension culture or an adherent culture.

The podocyte cultures described herein are suitable for medium- to high-throughput screening, among other purposes. Accordingly, the partially-differentiated podocytes can be reseeded into second cell cultures that are in any desired format suitable for screening or other purposes. For screening, the partially-differentiated podocytes can be reseeded into an array of second cell cultures, for example in a multiwall plate. The multi-well plate can be suitable for high throughput screening, including, e.g., 96-well plates, 384-well plates, or 1536-well plates.

4. Screening

A. Screening of Candidate Compounds

The podocyte cultures described herein can be used to screen candidate compounds for treating a kidney disease.

In one aspect, the invention provides a method of identifying a candidate compound for treating a kidney disease. In a general aspect, the method comprises: (a) providing a culture of terminally differentiated podocytes; (b) contacting a candidate compound with said terminally differentiated podocyte(s); and (c) determining a cellular or physiological characteristic of the terminally differentiated podocyte(s). A change in the cellular or physiological characteristic relative to a suitable control is indicative that said compound is a candidate for treating a kidney disease. Suitable cellular or physiological characteristics include, e.g., membrane permeability, morphology, viability, or expression of a podocyte marker.

In more particular aspects, the method comprises (a) providing an array comprising a plurality of units (e.g. cultures), each unit (e.g. culture) comprising one or more terminally differentiated podocytes; (b) contacting a candidate compound with said terminally differentiated podocyte(s) in at least one unit (e.g. cultures) of the array; and (c) determining a cellular characteristic of the terminally differentiated podocyte(s). A change in the cellular characteristic relative to a suitable control is indicative that said compound is a candidate for treating a kidney disease. Suitable cellular characteristics include, e.g., membrane permeability, morphology, viability, or expression of a podocyte marker. Preferably, substantially all of the units (e.g. cultures) in the array are either controls or are contacted with the same or different candidate compound.

In certain embodiments, the cellular or physiological characteristic is the healthiness of the terminally-differentiated podocyte, which is determined using the parameters described herein in section B.

In certain embodiments, the array comprises a multi-well plate, each well comprising one or more terminally differentiated podocytes.

A variety of controls may be used for this method. The corresponding cellular or physiological characteristic from a known healthy podocyte may be used as a control. The control may be cellular or physiological characteristic from a parallel assay in which the podocyte is cultured in the absence of the candidate compound. Still other suitable controls may be data or cellular characteristics that are present in a database or in publications. Generally, the suitable control is obtained form a culture that is not exposed to the candidate compound but is optionally exposed to any solvent, vehicle or diluent that is used to test the candidate compound.

B. Assessing the Healthiness of Podocytes

In another aspect, the invention provides a method of identifying healthy podocytes, such as terminally-differentiated podocytes including those produced by the culture methods described herein. In preferred embodiments, the method is used to identify healthy podocytes (e.g., terminally-differentiated podocytes) in a culture, such as the cultures described herein. The method comprises determining one or more of the parameters described in sections B1-B6 either individually or any desired combinations.

1. Average F-Actin Stress Fiber Fluorescent Intensity Ratio.

One parameter for identifying healthy podocytes is the average fluorescent intensity ratio of F-actin stress fibers over the whole cell by immunofluorescence, using an F-actin-specific agents (such as phalloidin, an F-actin-specific antibody or antigen-binding fragment thereof, or LifeAct (see; Riedl J, et al. Lifeact: a versatile marker to visualize F-actin. Nat Methods. 2008 July; 5(7):605-7. doi: 10.1038/nmeth.1220)). The F-actin-specific agent is conjugated to a fluorescent moiety.

In one standard assay, F-actin stress fibers are sectioned based upon a threshold of fluorescence intensity (Columbus "find spots" block, method B, detection sensitivity of about 0.4, splitting coefficient of about 0.505). This intensity ratio is calculated as the ratio of the mean intensity above the background from all pixels of all sectioned F-actin stress fibers of a cell and then divided by the background intensity of the cell. In one case, the fluorescence intensity is determined by pixel saturation of the fluorophore alexa fluor 594 with appropriate lasers and filters. In one example, an average fluorescent intensity ratio less than about 0.75 using actin cytoskeleton measurements and using Alexa fluor 594 as the fluorophore is indicative of a healthy podocyte. Acceptable upper limit of the average fluorescent intensity ratio for identifying healthy podocytes ranges from about 0.6 to 0.9. If a different fluorescent moiety that has different exit/emit wavelengths is used, the ratio can be adjusted based on the rationales provided herein.

2. The Average Number of Sectioned F-Actin Stress Fibers.

Another parameter for identifying healthy podocytes is counting the average number of sectioned F-actin stress fibers. F-actin stress fibers can be detected by immunofluorescence, using an F-actin-specific agents (such as phalloidin, F-actin-specific antibody or LifeAct) conjugated to a fluorescent moiety, such as Alexa fluor 594. F-actin stress fibers are sectioned based upon a threshold of fluorescence intensity (for example, using "find spots" block, method B, in Columbus software). A typical detection threshold uses a sensitivity value of 0.4 and a splitting coefficient of 0.505. Using this method, and when counted per cell, at least about 100 sectioned F-actin stress fibers per cell is indicative of a healthy podocyte. Acceptable lower limit of F-actin stress fibers per cell for identifying healthy podocytes ranges from at least about 80 to at least about 120 sectioned F-actin stress fibers per cell.

Average number of sectioned F-actin stress fibers per well can similarly be used, where at least about 100,000 F-actin stress fibers per well of a 96-well plate (typically with a surface area of about 0.32 $cm^2$ per well) are indicative of healthy podocytes. Acceptable lower limit of F-actin stress fibers per well for identifying healthy podocytes ranges from at least about 80,000 to at least about 120,000 sectioned F-actin stress fibers per well of a 96-well plate (typically with a surface area of about 0.32 $cm^2$ per well).

3. The Average Actin Fiber Area Per Cell.

Another parameter for identifying healthy podocytes is the total area of sectioned F-actin stress fibers per cell. F-actin stress fibers can be detected by immunofluorescence, using an F-actin-specific agents (such as phalloidin, F-actin-specific antibody or LifeAct) conjugated to a fluorescent moiety, such as Alexa fluor 594. F-actin stress fibers are sectioned based upon a threshold of fluorescence intensity (for example, using "find spots" block, method B, in Columbus software). A typical detection threshold uses a sensitivity value of 0.4 and a splitting coefficient of 0.505. Using this method, and when counted per cell, an average area of actin cytoskeleton of at least about 2000 $um^2$ per cell is indicative of a healthy podocyte. Acceptable lower limit of average area of actin cytoskeleton for identifying healthy podocytes ranges from at least about 1600 $um^2$ per cell to at least about 2400 $um^2$ per cell.

4. Average Podocyte Focal Adhesion Fluorescence Intensity Ratio.

Another parameter for identifying healthy podocytes is the fluorescence intensity ratio of focal adhesions over the whole cell intensity by immunofluorescence, using focal adhesion protein specific antibodies, such as a paxillin-specific antibody or a vinculin specific antibody. Such antibodies can be labeled with a fluorophore, or can be further detected by a second antibody conjugated to a fluorescence moiety. Focal adhesions are sectioned based upon a threshold of fluorescence intensity (for example, using "find spots" block, method B, in Columbus software). A typical detection threshold uses a sensitivity value of 0.4 and a splitting coefficient of 0.505. The focal adhesion fluorescence intensity ratio is calculated as the ratio of the mean intensity above the background from all pixels of all sectioned focal adhesions of a cell and then divided by the background intensity of the cell. In one case, the fluorescence intensity was determined by pixel saturation of the fluorophore alexa fluor 488 using the appropriate lasers and filters. Using this method, and when counted per cell, a fluorescence intensity ratio less than 0.835 using focal adhesion measurements is indicative of a healthy podocyte. Acceptable upper limit of the average fluorescent intensity ratio for identifying healthy podocytes ranges from about 0.668 to 1.002. If a different fluorescent moiety that has different exit/emit wavelengths is used, the ratio can be adjusted based on the rationales provided herein.

5. Average Number of Podocyte Focal Adhesions.

Another parameter for identifying healthy podocytes is the average number of podocyte focal adhesions by immunofluorescence, using focal adhesion protein specific antibodies, such as a paxillin-specific antibody or a vinculin specific antibody. Such antibodies can be directly labeled with a fluorophore or can be further detected by an antibody conjugated to a fluorescence moiety. Focal adhesions are sectioned based upon a threshold of fluorescence intensity (for example, using "find spots" block, method B, in Columbus software). A typical detection threshold uses a sensitivity value of 0.4 and a splitting coefficient of 0.505. The average number of focal adhesions is calculated as the number of focal adhesions with mean intensity above the background from all pixels of all sectioned focal adhesions of a cell. In one case, the fluorescence intensity was determined by pixel saturation of the fluorophore alexa fluor 488 using the appropriate lasers and filters. Using this method, and when counted per cell, an average of at least about 100 sectioned focal adhesions per cell is indicative of a healthy podocyte. Acceptable lower limit of sectioned focal adhesions per cell for identifying healthy podocytes ranges from at least about 80 sectioned focal adhesions per cell to about 120 sectioned focal adhesions per cell.

Average number of sectioned focal adhesions per well can similarly be used, where an average of at least about 280,000 sectioned focal adhesions per well of a 96-well plate (typically with a surface area of about 0.32 $cm^2$ per well) is indicative of a healthy podocyte. Acceptable lower limit of sectioned focal adhesions per well for identifying healthy podocytes ranges from at least about 224,000 sectioned focal adhesions per well to about 336,000 sectioned focal adhesions per well.

6. Average Podocyte Cell Roundedness.

Another parameter for identifying healthy podocytes is the average roundedness of the cell. Cell morphology can be determined by detecting nuclei/cytoplasm of a cell using immunofluorescence (for example, CellMask Blue fluorescent dye) and using the "Find Nuclei" analysis module of the Columbus software with method C and a common threshold of between 0.85 to 0.90 and an area greater than between 190 square micrometers to 250 micrometers. The cytoplasm can be detected using the "Find Cytoplasm" analysis module with method D and an individual threshold of 0.20. Based on these parameters, in one example, average cell roundedness was calculated using the "calculate morphology properties" building block. Using this method, an average podocyte cell roundedness value of less than 0.7 is indicative of healthy podocytes. Acceptable upper limit of average podocyte cell roundedness value for identifying healthy podocytes ranges from about 0.56 to about 0.84.

C. Diagnosis of Kidney Disease

The invention also relates to the diagnosis of kidney diseases or a predisposition to kidney disease in a patient.

In one aspect, podocytes from a subject may be cultured using methods described herein, and the cellular characteristic (such as healthiness) of the podocytes can be determined using methods described herein. The presence of unhealthy podocytes from the subject (e.g., in a terminally differentiated podocyte population produced using the methods described herein) is indicative that the subject has or is predisposed to a kidney disease.

In another aspect, serum or other suitable biological sample (e.g., bodily fluid) obtained from a subject to be diagnosed or screened. The serum of suitable biological sample is added to a culture of podocytes (e.g., a terminally differentiated podocyte population produced using the methods described herein) and after a sufficient period of time, the healthiness of the podocytes is determined using methods described herein. The presence of unhealthy podocytes in the culture is indicative that the subject has or is susceptible to a kidney disease. Generally, the podocytes are cultured with the serum or other suitable biological sample for at least about 6 hours, preferably at least about 12 hours or at least about 24 hours.

Exemplification

The invention now being generally described, it will be more readily understood by reference to the following examples, which are included merely for purposes of illustration of certain aspects and embodiments of the present invention, and are not intended to limit the invention.

Introduction

Cultured podocytes provide a validated model system that reliably recapitulates critical aspects of rodent and human glomerular disease. However, culturing podocytes in vitro has long been hampered by a number of issues that have hampered their use in a medium- or high-throughput assay environment. Podocytes show heterogeneous morphology in culture in vitro that makes it hard to get robust, reproducible data with low-variability between different wells, plates and on different days. Podocyte cell number is also highly variable from well-to-well and plate-to-plate, because of the long culture time needed to grow and appropriately differentiate these cells in vitro. Additionally, differentiated podocytes have shown limited ability to propagate in currently used cell culture system. These and other issues have prevented the adaption of these cells for use in a medium- or high-throughput assay environment such that high-throughput screening (HTS) and other such assays can be performed with these cells for the discovery of new drugs and drug candidates, signaling pathways, and in diagnosing disease by, for example, treating these cells with diseased patient fluids.

Previous research has shown that podocyte injury is reflected in increased podocyte cell death, increased motility of cultured cells and a loss of actin stress fibers (parallel actin bundles) in cells. Thus, a rescue of such cellular "phenotypes" or function has been suggested as a way to determine and identify potential therapeutic agents. Rescue of actin stress fibers in vitro has also correlated well with protection from FP effacement and proteinuria in vivo in a select few published studies. Additionally, reporter-based assays can serve to identify podocyte-targeting drugs. Yamauchi et al. used immortalized murine podocytes stably transfected with a reporter gene encoding secreted alkaline phosphatase under the control of the nephrin promoter (Yamauchi K, Takano Y, Kasai A et al. Screening and identification of substances that regulate nephrin gene expression using engineered reporter podocytes. Kidney Int 2006; 70: 892-900). The established reporter cells were exposed to various substances, and culture media were subjected to a secreted alkaline phosphatase assay to identify regulators of nephrin gene expression. An inherent problem of quantitative reporter-based assays, however, is the long duration required for cultured podocytes to fully differentiate, which could potentially also lead to high well-to-well and plate-to-plate variability. Here, we have also made significant improvements in how the cells are quantitatively analyzed.

We developed assays and methods that are suitable for adapting podocytes for use in medium- and high-throughput assay environments. Unique culturing techniques, assay methods, image analysis methods and algorithms were used. We have also optimized the methods for culturing these cells in vitro for the specific purpose of use in medium- and high-throughput assays. As described in FIG. 1, first, the cells were grown in larger cell culture dishes and then transfered into multiwall plates for use in the medium- and high-throughput assays. Second, we partially differentiated these cells in the large culture dishes and subsequently complete their differentiation in the multi-well plates. These steps result in robust, reproducible, and homogenous cells in the multiwall plates. These steps also significantly improved the quality of the cellular morphology so that the well-to-well and plate-to-plate variability is also low.

Previously described handling methods call for the immortal mouse podocyte cell line to be differentiated for 14 days in plates, whereas we found that cell re-seeding of partially differentiated cells, which followed with a podocyte assay, can be used to achieve or control homogeneity and phenotype.

We have also made significant improvements in how the cells are quantitatively analyzed. We have developed image analysis methods to determine podocyte health using specific measurements of the actin cytoskeleton, focal adhesions, and morphology of the podocyte in vitro. In one approach, we quantitated the changes in podocytes that are induced by treatment with a damaging agent or with an agent to maintain or improve podocyte health, using a high content approach based on focal adhesions and/or the actin cytoskeleton. In another approach, we quantitated the changes in podocytes using multiple parameters to better segregate different population subtypes in a single well.

Additionally, averaging data over multiple wells and multiple cells and normalizing the data to represent values as average/cell greatly improved the overall data quality and statistics.

Results

Changes in the podocyte actin cytoskeleton were measured by the intensity and number of F-actin stress fibers. The F-actin stress fibers were sectioned from the image and contrasted to the intensity of the rest of the cell to give a ratio of intensities. The intensity ratio of the F-actin stress fibers to the cell along with the number of sectioned F-actin stress fibers per cell were able to quantitate changes in the podocyte induced by PAN. Changes in the podocytes focal adhesions were also monitored using the previously mentioned parameters and were also able to quantitate changes in a dose response fashion to PAN. Also, the aforementioned parameters for quantitation of the podocyte actin cytoskeleton and focal adhesion were also found to measure in a dose response fashion the protection from PAN treatment by Mizouribine.

Additionally, these parameters were found to better differentiate a healthy podocyte phenotype from a damaged podocyte phenotype when combined. One example of multiparametric analysis would be a two dimensional comparison between the sectioned F-actin stress fibers intensity to the cell versus the cell's total area of sectioned F-actin stress fibers to sort cells into populations of healthy versus damaged cells. This multiparametric method was found to increase the sensitivity of the assay over using one parameter. Overall this assay is a robust quantitative method to determine in-vitro podocyte health and is a marked improvement over the current art of the field which is qualitative observation of podocyte health.

Methods

Podocyte Cell Culture

Human and murine podocytes were cultured as have been described previously (Saleem et al., JASN 13, 630-638 (2002); Mundel, Reiser et al., Experimental Cell Research, 236, p 248 (1997)). For example, murine podocytes derived from the mouse line H-2K$^b$-tsA58 were cultured under permissive conditions at 33° C. on rat-tail collagen coated dishes in RPMI medium supplemented with 10% heat inactivated FBS, penicillin and streptomycin (100 U/ml), and 10 U/ml recombinant mouse γ-interferon. Cells were then trypsinized and re-plated for differentiation at 37° C. in medium without γ-interferon. The cells were differentiated for 0 to 7 days and then reseeded to rat-tail collagen coated multi-well plates at a density of 1500/well or 500/well for 96 and 384 well plates, respectively. Cells were then further differentiated for another 5-14 days in the multi-well plates for subsequent experimentation with various reagents prior to fixation and analyses. Methods for isolating and culturing primary podocytes are well known in the art. For example, see: Kabgani et al., Primary Cultures of Glomerular Parietal Epithelial Cells or Podocytes with Proven Origin, Plos One, PLoS ONE (2012) 7(4): e34907. doi:10.1371/journal.pone.0034907.

Fluorescence Microscopy

Differentiated podocytes were cultured in 96-well or 384-well multiwall optical plates (PerkinElmer, Boston, Mass.) and treated with various amounts of puromycin, PAN, LPS, Adriamycin and other agents. In some cases, the cells were co-treated with chemical and other agents (such as mizouribine) to prevent damage from damaging agents (such as PAN). In other cases, the rescue agents were added 0-48 h after the addition of injury causing agents. Subsequently, the cells were fixed with a solution containing a 4% paraformaldehyde and 2% sucrose (added directly to cell culture media, without disturbing the cells or removing the culture media) 1 hour followed by permeabilization with 0.3% Triton X-100 in PBS for 10 min at room temperature. F-actin was visualized with Alexa fluor 594 phalloidin (Invitrogen), HCS CellMask Blue (Invitrogen) was used for a nuclear/cytoplasmic stain, and anti-Paxillin antibody clone Y113 was used for detecting focal adhesions. The anti-paxillin antibody was further detected using alexa fluor 488 conjugated secondary antibody. Confocal microscopy was performed using the Opera XL (Perkin Elmer) with appropriate filters. Images were used in subsequent image analysis for quantitation of a variety of cellular parameters. Assays were performed in replicate wells for assay robustness.

Image Analysis

Images were analyzed using Columbus 2.3.2 high-content screening image data storage and analysis system (PerkinElmer). The CellMask Blue stained nuclei were detected using the "Find Nuclei" analysis module with method C and a common threshold of between 0.85 to 0.90 and an area greater than between 190 square micometers to 250 square micometers. The cytoplasm was detected using the "Find Cytoplasm" analysis module with method D and an individual threshold of 0.20. Cells for analysis were selected with a minimum mean cell intensity of 100 and 1500 um$^2$ for cell area. F-actin fibers were sectioned using the "Find Spots" analysis module with method B and detection sensitivity and splitting coefficients of 0.40 and 0.505, respectively. In some cases, splitting coefficients of 0.45 and 0.46, respectively, were applied. Healthy versus damaged cell populations were sorted by the parameters "Relative Spot to Background Intensity" and "Total Spot Area" parameters using the "Select Populations" analysis module. Healthy versus damaged cell populations were then used for determining the percentage of healthy cells per well. Approximately 100 to 1500 cells per well were analyzed.

For statistical analyses, Data were analyzed using GraphPad Prism and Microsoft Excel with advanced analysis add-in and were compared using student's t-test. P-values<0.05 were considered significant.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents and NCBI Entrez or gene ID sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A method of culturing podocytes in vitro, comprising:
   (a) maintaining a podocyte cell in a first cell culture under a permissive condition or proliferation condition for a period of time sufficient for the podocyte cell to double at least once, thereby producing a population of podocytes;
   (b) maintaining the population of podocytes obtained in a) under a non-permissive condition or differentiation condition for a period of time sufficient to obtain a population of partially differentiated podocytes; and
   (c) re-seeding the partially differentiated podocytes obtained in b) and maintaining the partially differentiated podocytes obtained in b) in a second cell culture under a non-permissive condition or differentiation condition for a period of time sufficient to obtain a population of terminally-differentiated podocytes.

2. The method of claim 1, wherein said second cell culture is contained within a multi-well plate.

3. The method of claim 2, wherein said multi-well plate is suitable for high throughput screening.

4. The method of claim 1, wherein said podocyte cell is maintained in an adherent culture.

5. The method of claim 1, wherein said podocyte cell is a conditionally-immortalized podocyte.

6. The method of claim 5, wherein said conditionally-immortalized podocyte is a murine cell or a human cell.

7. The method of claim 5, wherein in step (a), said population of podocytes are maintained in an adherent culture that is at least about 60% confluent.

8. The method claim 5, wherein in step (a), said conditionally-immortalized podocyte is maintained under the permissive condition for between about 5 days and about 20 days.

9. The method of claim 5, wherein in step (a), said conditionally-immortalized podocyte is maintained under the permissive condition for between about 7 days and about 14 days.

10. The method of claim 5, wherein in step (b), said population of podocytes are maintained under the non-permissive condition for between about 4 days and about 8 days.

11. The method of claim 5, wherein in step (c), said partially differentiated podocytes are maintained under the non-permissive condition for between about 5 days and about 20 days.

12. The method of claim 5, wherein in step (c), said partially differentiated podocytes are maintained under the non-permissive condition for between about 6 days and about 15 days.

13. A method of identifying a candidate compound for treating a kidney disease, comprising:
   (a) providing an array comprising a plurality of units, each unit comprising one or more terminally differentiated podocytes; the one or more terminally differentiated podocytes obtained by i) maintaining a podocyte cell in a first cell culture under a permissive condition or proliferation condition for a period of time sufficient for the podocyte cell to double at least once, thereby producing a population of podocytes; (ii) maintaining the population of podocytes obtained in i) under a non-permissive condition or differentiation condition for a period of time sufficient to obtain a population of partially differentiated podocytes; and (iii) re-seeding the partially differentiated podocytes obtained in ii) and maintaining the partially differentiated podocytes obtained in ii) in a second cell culture under a non-permissive condition or differentiation condition for a period of time sufficient to obtain the one or more of terminally differentiated podocytes;
   (b) contacting a candidate compound with said terminally differentiated podocyte(s) in at least one unit of the array; and
   (c) determining a cellular characteristic of the terminally differentiated podocyte(s); wherein a change in the cellular characteristic relative to a suitable control is indicative that said compound is a candidate for treating a kidney disease.

14. The method of claim 13, wherein the cellular characteristic is membrane permeability, morphology, viability, or expression of a podocyte marker.

15. The method of claim 14, wherein said podocyte marker is F-actin.

16. The method claim 15, wherein the expression level of F-actin is determined by fluorescent staining, using an F-actin-specific binding agent conjugated to a fluorescent moiety.

17. The method of claim 15, wherein the expression level of F-actin is determined by ELISA or western blot.

18. The method of claim 14, wherein said morphology is the average length of the actin cytoskeleton.

19. The method of claim 18, wherein the cell morphology is analyzed by optical or electronic microscopy.

20. The method of claim 13, wherein said array comprises a multi-well plate, each well comprising one or more terminally differentiated podocytes.

21. The method of claim 13, wherein said candidate compound improves the viability of a terminally differentiated podocyte.

* * * * *